United States Patent
Wu et al.

(10) Patent No.: US 9,156,904 B2
(45) Date of Patent: Oct. 13, 2015

(54) THROMBOMODULIN VARIANTS AND USE THEREOF

(71) Applicant: Blue Blood Biotech Corp., Taipei (TW)

(72) Inventors: Hua-Lin Wu, Tainan (TW); Guey-Yueh Shi, Tainan (TW)

(73) Assignee: Blue Blood Biotech Corp., Taipei (TW)

( * ) Notice: Subject to any disclaimer, the term of this patent is extended or adjusted under 35 U.S.C. 154(b) by 0 days.

(21) Appl. No.: 14/340,698

(22) Filed: Jul. 25, 2014

(65) Prior Publication Data

US 2015/0031620 A1  Jan. 29, 2015

Related U.S. Application Data

(60) Provisional application No. 61/859,433, filed on Jul. 29, 2013.

(51) Int. Cl.
*C07K 14/745* (2006.01)
*A61K 38/36* (2006.01)
*A61K 38/00* (2006.01)

(52) U.S. Cl.
CPC ............. *C07K 14/7455* (2013.01); *A61K 38/00* (2013.01); *A61K 38/366* (2013.01)

(58) Field of Classification Search
None
See application file for complete search history.

(56) References Cited

U.S. PATENT DOCUMENTS

| | | | | |
|---|---|---|---|---|
| 5,583,102 A | * | 12/1996 | Lentz et al. | 514/13.7 |
| 8,293,710 B2 | * | 10/2012 | Wu et al. | 514/9.4 |
| 2003/0186883 A1 | * | 10/2003 | Light et al. | 514/12 |
| 2008/0051562 A1 | * | 2/2008 | Chaikof et al. | 530/381 |

OTHER PUBLICATIONS

Fuentes-Prior, Structural basis for the anticoagulant activity of the thrombin-thrombomodulin complex, Nature, vol. 404, Mar. 30, 2000, pp. 518-525.*

Nagashima et al., Alanine-scanning Mutagenesis of the Epidermal Growth Factor-like Domains of Human Thrombomodulin Identifies Crucial Residues for Its Cofactor Activity, Jl. Biol. Chem., vol. 268, No. 4, Feb. 5, 1993, pp. 2888-2892.*

* cited by examiner

*Primary Examiner* — Karlheinz R Skowronek
*Assistant Examiner* — Joseph Fischer
(74) *Attorney, Agent, or Firm* — Hsiu-Ming Saunders; Intellectual Property Connections, Inc.

(57) ABSTRACT

A pharmaceutical composition comprising an effective amount of a mutant thrombomodulin is disclosed. The mutant thrombomodulin comprises an amino acid sequence that is at least 80% identical to SEQ ID NO: 2 and has residues corresponding to $Ala^{364}$ and $Ala^{391}$ of SEQ ID NO: 2. The mutant thrombomodulin has little or no protein C activation activity, and is effective in promoting wound healing and accelerating closure of an open wound in a diabetic.

20 Claims, 9 Drawing Sheets

FIG. 1-1　　　　　　　　　　Wild-type TMD123

| gca | ccc | gca | gag | ccg | cag | ccg | ggt | ggc | agc | cag | tgc | gtc | gag | cac | gac | tgc | ttc | 54 |
|-----|-----|-----|-----|-----|-----|-----|-----|-----|-----|-----|-----|-----|-----|-----|-----|-----|-----|-----|
| Ala | Pro | Ala | Glu | Pro | Gln | Pro | Gly | Gly | Ser | Gln | Cys | Val | Glu | His | Asp | Cys | Phe | |
| 1 | | | | 5 | | | | | 10 | | | | | 15 | | | | |

| gcg | ctc | tac | ccg | ggc | ccc | gcg | acc | ttc | ctc | aat | gcc | agt | cag | atc | tgc | gac | gga | 108 |
|-----|-----|-----|-----|-----|-----|-----|-----|-----|-----|-----|-----|-----|-----|-----|-----|-----|-----|-----|
| Ala | Leu | Tyr | Pro | Gly | Pro | Ala | Thr | Phe | Leu | Asn | Ala | Ser | Gln | Ile | Cys | Asp | Gly | |
| | 20 | | | | 25 | | | | | 30 | | | | | 35 | | | |

| ctg | cgg | ggc | cac | cta | atg | aca | gtg | cgc | tcc | tcg | gtg | gct | gcc | gat | gtc | att | tcc | 162 |
|-----|-----|-----|-----|-----|-----|-----|-----|-----|-----|-----|-----|-----|-----|-----|-----|-----|-----|-----|
| Leu | Arg | Gly | His | Leu | Met | Thr | Val | Arg | Ser | Ser | Val | Ala | Ala | Asp | Val | Ile | Ser | |
| | | | 40 | | | | | 45 | | | | | 50 | | | | | |

| ttg | cta | ctg | aac | ggc | gac | ggc | gtt | ggc | cgc | cgg | cgc | ctc | tgg | atc | ggc | ctg | | 216 |
|-----|-----|-----|-----|-----|-----|-----|-----|-----|-----|-----|-----|-----|-----|-----|-----|-----|-----|-----|
| Leu | Leu | Leu | Asn | Gly | Asp | Gly | Val | Gly | Arg | Arg | Arg | Leu | Trp | Ile | Gly | Leu | | |
| 55 | | | | | 60 | | | | | 65 | | | | | 70 | | | |

| cag | ctg | cca | ccc | ggc | tgc | ggc | gac | ccc | aag | cgc | ctc | ggg | ccc | ctg | cgc | ggc | ttc | 270 |
|-----|-----|-----|-----|-----|-----|-----|-----|-----|-----|-----|-----|-----|-----|-----|-----|-----|-----|-----|
| Gln | Leu | Pro | Pro | Gly | Cys | Gly | Asp | Pro | Lys | Arg | Leu | Gly | Pro | Leu | Arg | Gly | Phe | |
| | | 75 | | | | | 80 | | | | | 85 | | | | | 90 | |

| cag | tgg | gtt | acg | gga | gac | aac | aac | acc | agc | tat | agc | agg | tgg | gca | cgg | ctc | gac | 324 |
|-----|-----|-----|-----|-----|-----|-----|-----|-----|-----|-----|-----|-----|-----|-----|-----|-----|-----|-----|
| Gln | Trp | Val | Thr | Gly | Asp | Asn | Asn | Thr | Ser | Tyr | Ser | Arg | Trp | Ala | Arg | Leu | Asp | |
| | | | 95 | | | | | 100 | | | | | 105 | | | | | |

| ctc | aat | ggg | gct | ccc | ctc | tgc | ggc | ccg | ttg | tgc | gtc | gct | gtc | tcc | gct | gct | gag | 378 |
|-----|-----|-----|-----|-----|-----|-----|-----|-----|-----|-----|-----|-----|-----|-----|-----|-----|-----|-----|
| Leu | Asn | Gly | Ala | Pro | Leu | Cys | Gly | Pro | Leu | Cys | Val | Ala | Val | Ser | Ala | Ala | Glu | |
| | 110 | | | | 115 | | | | | 120 | | | | | 125 | | | |

| gcc | act | gtg | ccc | agc | gag | ccg | atc | tgg | gag | gag | cag | cag | tgc | gaa | gtg | aag | gcc | 432 |
|-----|-----|-----|-----|-----|-----|-----|-----|-----|-----|-----|-----|-----|-----|-----|-----|-----|-----|-----|
| Ala | Thr | Val | Pro | Ser | Glu | Pro | Ile | Trp | Glu | Glu | Gln | Gln | Cys | Glu | Val | Lys | Ala | |
| | | | 130 | | | | | 135 | | | | | 140 | | | | | |

| gat | ggc | ttc | ctc | tgc | gag | ttc | cac | ttc | cca | gcc | acc | tgc | agg | cca | ctg | gct | gtg | 486 |
|-----|-----|-----|-----|-----|-----|-----|-----|-----|-----|-----|-----|-----|-----|-----|-----|-----|-----|-----|
| Asp | Gly | Phe | Leu | Cys | Glu | Phe | His | Phe | Pro | Ala | Thr | Cys | Arg | Pro | Leu | Ala | Val | |
| 145 | | | | | 150 | | | | | 155 | | | | | 160 | | | |

| gag | ccc | ggc | gcc | gcg | gct | gcc | gcc | gtc | tcg | atc | acc | tac | ggc | acc | ccg | ttc | gcg | 540 |
|-----|-----|-----|-----|-----|-----|-----|-----|-----|-----|-----|-----|-----|-----|-----|-----|-----|-----|-----|
| Glu | Pro | Gly | Ala | Ala | Ala | Ala | Ala | Val | Ser | Ile | Thr | Tyr | Gly | Thr | Pro | Phe | Ala | |
| | | | 165 | | | | | 170 | | | | | 175 | | | | | 180 |

| gcc | cgc | gga | gcg | gac | ttc | cag | gcg | ctg | ccg | gtg | ggc | agc | tcc | gcc | gcg | gtg | gct | 594 |
|-----|-----|-----|-----|-----|-----|-----|-----|-----|-----|-----|-----|-----|-----|-----|-----|-----|-----|-----|
| Ala | Arg | Gly | Ala | Asp | Phe | Gln | Ala | Leu | Pro | Val | Gly | Ser | Ser | Ala | Ala | Val | Ala | |
| | | | | 185 | | | | | 190 | | | | | 195 | | | | |

FIG. 1-2

| | | | | | | | | | | | | | | | |
|---|---|---|---|---|---|---|---|---|---|---|---|---|---|---|---|
| ccc | ctc | ggc | tta | cag | cta | atg | tgc | acc | gcg | ccc | gga | gcg | gtc | cag | ggg | cac | 648 |
| Pro | Leu | Gly | Leu | Gln | Leu | Met | Cys | Thr | Ala | Pro | Pro | Gly | Ala | Val | Gln | Gly | His |
| | | 200 | | | | 205 | | | | 210 | | | | 215 | | | | tgg gcc agg gag gcg ccg ggc                                                                          669
Trp Ala Arg Glu Ala Pro Gly
              220 gct tgg gac tgc agc gtg gag aac ggc ggc tgc gag cac gcg tgc aat gcg atc       723
Ala Trp Asp Cys Ser Val Glu Asn Gly Gly Cys Glu His Ala Cys Asn Ala Ile
    225                 230                 235                 240 cct ggg gct ccc cgc tgc cag tgc cca gcc ggc gcc ctg cag gca gac ggg          777
Pro Gly Ala Pro Arg Cys Gln Cys Pro Ala Gly Ala Ala Leu Gln Ala Asp Gly
        245                 250                 255 cgc tcc tgc acc gca tcc gcg acg cag tcc tgc aac gac ctc tgc gag cac ttc     831
Arg Ser Cys Thr Ala Ser Ala Thr Gln Ser Cys Asn Asp Leu Cys Glu His Phe
260                 265                 270                 275 tgc gtt ccc aac ccc gac cag ccg ggc tcc tac tcg tgc atg tgc gag acc ggc     885
Cys Val Pro Asn Pro Asp Gln Pro Gly Ser Tyr Ser Cys Met Cys Glu Thr Gly
        280                 285                 290                 295 tac cgg ctg gcg gcc gac caa cac cgg tgc gag gac gtg gat gac tgc ata ctg     939
Tyr Arg Leu Ala Ala Asp Gln His Arg Cys Glu Asp Val Asp Asp Cys Ile Leu
        300                 305                 310 gag ccc agt ccg tgt ccg cag cgc tgt gtc aac aca cag ggt ggc ttc gag tgc     993
Glu Pro Ser Pro Cys Pro Gln Arg Cys Val Asn Thr Gln Gly Gly Phe Glu Cys
    315                 320                 325                 330 cac tgc tac cct aac tac gac ctg gtg gac ggc gag tgt gtg gag ccc gtg gac    1047
His Cys Tyr Pro Asn Tyr Asp Leu Val Asp Gly Glu Cys Val Glu Pro Val Asp
            335                 340                 345 ccg tgc ttc aga gcc aac tgc gag tac cag tgc cag ccc ctg aac caa act agc   1101
Pro Cys Phe Arg Ala Asn Cys Glu Tyr Gln Cys Gln Pro Leu Asn Gln Thr Ser
350                 355                 360                 365 tac ctc tgc gtc tgc gcc gag ggc ttc gcg ccc att ccc cac gag ccg cac agg   1155
Tyr Leu Cys Val Cys Ala Glu Gly Phe Ala Pro Ile Pro His Glu Pro His Arg
        370                 375                 380                 385

FIG. 1-3

| | | | | | | | | | | | | | | | | |
|---|---|---|---|---|---|---|---|---|---|---|---|---|---|---|---|---|
| tgc | cag | atg | ttt | tgc | aac | cag | act | gcc | tgt | cca | gcc | gac | tgc | gac | ccc | aac | acc | 1209 |
| Cys | Gln | Met | Phe | Cys | Asn | Gln | Thr | Ala | Cys | Pro | Ala | Asp | Cys | Asp | Pro | Asn | Thr |
| | | | | 390 | | | | 395 | | | | | 400 | | | |

| cag | gct | agc | tgt | gag | tgc | cct | gaa | ggc | tac | atc | ctg | gac | gac | ggt | ttc | atc | tgc | 1263 |
| Gln | Ala | Ser | Cys | Glu | Cys | Pro | Glu | Gly | Tyr | Ile | Leu | Asp | Asp | Gly | Phe | Ile | Cys |
| | 405 | | | | 410 | | | | 415 | | | | 420 | | | |

| acg | gac | atc | gac | gag | tgc | gaa | aac | ggc | ggc | ttc | tgc | tcc | ggg | gtg | tgc | cac | aac | 1317 |
| Thr | Asp | Ile | Asp | Glu | Cys | Glu | Asn | Gly | Gly | Phe | Cys | Ser | Gly | Val | Cys | His | Asn |
| | | 425 | | | | 430 | | | | 435 | | | | | | |

| ctc | ccc | ggt | acc | ttc | gag | tgc | atc | tgc | ggg | ccc | gac | tcg | gcc | ctt | gtc | cgc | cac | 1371 |
| Leu | Pro | Gly | Thr | Phe | Glu | Cys | Ile | Cys | Gly | Pro | Asp | Ser | Ala | Leu | Val | Arg | His |
| 440 | | | | | 445 | | | | 450 | | | | | 455 | | |

| att | ggc | acc | gac | tgt | gac | tcc | ggc | aag | gtg | gac | ggt | ggc | gac | agc | ggc | tct | ggc | 1425 |
| Ile | Gly | Thr | Asp | Cys | Asp | Ser | Gly | Lys | Val | Asp | Gly | Gly | Asp | Ser | Gly | Ser | Gly |
| | | 460 | | | | 465 | | | | 470 | | | | 475 | | |

| gag | ccc | ccg | ccc | agc | ccg | acg | ccc | ggc | tcc | acc | ttg | act | cct | ccg | gcc | gtg | ggg | 1479 |
| Glu | Pro | Pro | Pro | Ser | Pro | Thr | Pro | Gly | Ser | Thr | Leu | Thr | Pro | Pro | Ala | Val | Gly |
| | | | | 480 | | | | 485 | | | | | 490 | | | |

| ctc | gtg | cat | tcg | ggc | ttg | ctc | ata | ggc | atc | tcc | atc | gcg | agc | ctg | tgc | ctg | gtg | 1533 |
| Leu | Val | His | Ser | Gly | Leu | Leu | Ile | Gly | Ile | Ser | Ile | Ala | Ser | Leu | Cys | Leu | Val |
| | 495 | | | | 500 | | | | 505 | | | | 510 | | | |

| gtg | gcg | ctt | ttg | gcg | ctc | ctc | tgc | cac | ctg | cgc | aag | aag | cag | ggc | gcc | gcc | agg | 1587 |
| Val | Ala | Leu | Leu | Ala | Leu | Leu | Cys | His | Leu | Arg | Lys | Lys | Gln | Gly | Ala | Ala | Arg |
| | | | 515 | | | | 520 | | | | 525 | | | | | |

| gcc | aag | atg | gag | tac | aag | tgc | gcg | gcc | cct | tcc | aag | gag | gta | gtg | ctg | cag | cac | 1641 |
| Ala | Lys | Met | Glu | Tyr | Lys | Cys | Ala | Ala | Pro | Ser | Lys | Glu | Val | Val | Leu | Gln | His |
| 530 | | | | | 535 | | | | 540 | | | | | 545 | | |

| gtg | cgg | acc | gag | cgg | acg | ccg | cag | aga | ctc | | | | | | | | | 1671 |
| Val | Arg | Thr | Glu | Arg | Thr | Pro | Gln | Arg | Leu |
| | 550 | | | | 555 | | | | |

FIG. 2-1  Mutant TMD123

| gca | ccc | gca | gag | ccg | cag | ccg | ggt | ggc | agc | cag | tgc | gtc | gag | cac | gac | tgc | ttc | 54 |
|---|---|---|---|---|---|---|---|---|---|---|---|---|---|---|---|---|---|---|
| Ala | Pro | Ala | Glu | Pro | Gln | Pro | Gly | Gly | Ser | Gln | Cys | Val | Glu | His | Asp | Cys | Phe | |
| 1 | | | | 5 | | | | | 10 | | | | | 15 | | | | |

| gcg | ctc | tac | ccg | ggc | ccc | gcg | acc | ttc | ctc | aat | gcc | agt | cag | atc | tgc | gac | gga | 108 |
|---|---|---|---|---|---|---|---|---|---|---|---|---|---|---|---|---|---|---|
| Ala | Leu | Tyr | Pro | Gly | Pro | Ala | Thr | Phe | Leu | Asn | Ala | Ser | Gln | Ile | Cys | Asp | Gly | |
| | 20 | | | | 25 | | | | | 30 | | | | | 35 | | | |

| ctg | cgg | ggc | cac | cta | atg | aca | gtg | cgc | tcc | tcg | gtg | gct | gcc | gat | gtc | att | tcc | 162 |
|---|---|---|---|---|---|---|---|---|---|---|---|---|---|---|---|---|---|---|
| Leu | Arg | Gly | His | Leu | Met | Thr | Val | Arg | Ser | Ser | Val | Ala | Ala | Asp | Val | Ile | Ser | |
| | | | 40 | | | | | 45 | | | | | 50 | | | | | |

| ttg | cta | ctg | aac | ggc | gac | ggc | ggc | gtt | ggc | cgc | cgg | cgc | ctc | tgg | atc | ggc | ctg | 216 |
|---|---|---|---|---|---|---|---|---|---|---|---|---|---|---|---|---|---|---|
| Leu | Leu | Leu | Asn | Gly | Asp | Gly | Gly | Val | Gly | Arg | Arg | Arg | Leu | Trp | Ile | Gly | Leu | |
| 55 | | | | | 60 | | | | | 65 | | | | | 70 | | | |

| cag | ctg | cca | ccc | ggc | tgc | ggc | gac | ccc | aag | cgc | ctc | ggg | ccc | ctg | cgc | ggc | ttc | 270 |
|---|---|---|---|---|---|---|---|---|---|---|---|---|---|---|---|---|---|---|
| Gln | Leu | Pro | Pro | Gly | Cys | Gly | Asp | Pro | Lys | Arg | Leu | Gly | Pro | Leu | Arg | Gly | Phe | |
| | | | 75 | | | | | 80 | | | | | 85 | | | | | 90 |

| cag | tgg | gtt | acg | gga | gac | aac | aac | acc | agc | tat | agc | agg | tgg | gca | cgg | ctc | gac | 324 |
|---|---|---|---|---|---|---|---|---|---|---|---|---|---|---|---|---|---|---|
| Gln | Trp | Val | Thr | Gly | Asp | Asn | Asn | Thr | Ser | Tyr | Ser | Arg | Trp | Ala | Arg | Leu | Asp | |
| | | | | 95 | | | | | 100 | | | | | 105 | | | | |

| ctc | aat | ggg | gct | ccc | ctc | tgc | ggc | ccg | ttg | tgc | gtc | gct | gtc | tcc | gct | gct | gag | 378 |
|---|---|---|---|---|---|---|---|---|---|---|---|---|---|---|---|---|---|---|
| Leu | Asn | Gly | Ala | Pro | Leu | Cys | Gly | Pro | Leu | Cys | Val | Ala | Val | Ser | Ala | Ala | Glu | |
| | 110 | | | | 115 | | | | | 120 | | | | | 125 | | | |

| gcc | act | gtg | ccc | agc | gag | ccg | atc | tgg | gag | gag | cag | cag | tgc | gaa | gtg | aag | gcc | 432 |
|---|---|---|---|---|---|---|---|---|---|---|---|---|---|---|---|---|---|---|
| Ala | Thr | Val | Pro | Ser | Glu | Pro | Ile | Trp | Glu | Glu | Gln | Gln | Cys | Glu | Val | Lys | Ala | |
| | | | 130 | | | | | 135 | | | | | 140 | | | | | |

| gat | ggc | ttc | ctc | tgc | gag | ttc | cac | ttc | cca | gcc | acc | tgc | agg | cca | ctg | gct | gtg | 486 |
|---|---|---|---|---|---|---|---|---|---|---|---|---|---|---|---|---|---|---|
| Asp | Gly | Phe | Leu | Cys | Glu | Phe | His | Phe | Pro | Ala | Thr | Cys | Arg | Pro | Leu | Ala | Val | |
| 145 | | | | | 150 | | | | | 155 | | | | | 160 | | | |

| gag | ccc | ggc | gcc | gcg | gct | gcc | gcc | gtc | tcg | atc | acc | tac | ggc | acc | ccg | ttc | gcg | 540 |
|---|---|---|---|---|---|---|---|---|---|---|---|---|---|---|---|---|---|---|
| Glu | Pro | Gly | Ala | Ala | Ala | Ala | Ala | Val | Ser | Ile | Thr | Tyr | Gly | Thr | Pro | Phe | Ala | |
| | | | 165 | | | | | 170 | | | | | 175 | | | | | 180 |

| gcc | cgc | gga | gcg | gac | ttc | cag | gcg | ctg | ccg | gtg | ggc | agc | tcc | gcc | gcg | gtg | gct | 594 |
|---|---|---|---|---|---|---|---|---|---|---|---|---|---|---|---|---|---|---|
| Ala | Arg | Gly | Ala | Asp | Phe | Gln | Ala | Leu | Pro | Val | Gly | Ser | Ser | Ala | Ala | Val | Ala | |
| | | | | 185 | | | | | 190 | | | | | 195 | | | | |

FIG. 2-2

| | | | | | | | | | | | | | | |
|---|---|---|---|---|---|---|---|---|---|---|---|---|---|---|
| ccc | ctc | ggc | tta | cag | cta | atg | tgc | acc | gcg | ccg | gga | gcg | gtc | cag | ggg | cac | 648 |
| Pro | Leu | Gly | Leu | Gln | Leu | Met | Cys | Thr | Ala | Pro | Gly | Ala | Val | Gln | Gly | His |
| | 200 | | | | | 205 | | | | | 210 | | | | | 215 | tgg gcc agg gag gcg ccg ggc                                                            669
Trp Ala Arg Glu Ala Pro Gly
                220 gca tgg gac tgc tca gtg gaa aac gga ggt tgc gaa cat gca tgt aac gcc atc               723
Ala Trp Asp Cys Ser Val Glu Asn Gly Gly Cys Glu His Ala Cys Asn Ala Ile
    225              230                  235                 240 cct ggt gcc cca aga tgt caa tgc cca gct ggg gct gca ctg caa gca gat ggc               777
Pro Gly Ala Pro Arg Cys Gln Cys Pro Ala Gly Ala Ala Leu Gln Ala Asp Gly
        245              250                  255 aga tct tgt act gct tcc gct aca caa tct tgt aac gat ttg tgt gaa cat ttt               831
Arg Ser Cys Thr Ala Ser Ala Thr Gln Ser Cys Asn Asp Leu Cys Glu His Phe
260             265                  270                 275 tgt gtt cca aat cca gac caa cct ggt tct tac tct tgc atg tgt gaa acg ggt               885
Cys Val Pro Asn Pro Asp Gln Pro Gly Ser Tyr Ser Cys Met Cys Glu Thr Gly
        280              285                  290                 295 tac aga ttg gct gcc gac caa cat aga tgt gag gat gtt gat gat tgt ata ttg               939
Tyr Arg Leu Ala Ala Asp Gln His Arg Cys Glu Asp Val Asp Asp Cys Ile Leu
    300                  305                 310 gaa cct agt cca tgt cct caa aga tgc gtc aac act caa ggt ggg ttc gaa tgc               993
Glu Pro Ser Pro Cys Pro Gln Arg Cys Val Asn Thr Gln Gly Gly Phe Glu Cys
    315                  320                 325                 330 cat tgc tac ccc aat tat gat ctg gtt gac ggt gag tgt gta gag cca gtc gat              1047
His Cys Tyr Pro Asn Tyr Asp Leu Val Asp Gly Glu Cys Val Glu Pro Val Asp
        335              340                  345 cct tgt ttc cga gcc aac tgt gag tac caa tgt cag cct ttg gct caa act agt              1101
Pro Cys Phe Arg Ala Asn Cys Glu Tyr Gln Cys Gln Pro Leu Ala Gln Thr Ser
350             355                  360             *   365 tac ctg tgt gtc tgt gca gag ggt ttc gct cct att cct cac gaa ccc cac aga              1155
Tyr Leu Cys Val Cys Ala Glu Gly Phe Ala Pro Ile Pro His Glu Pro His Arg
    370                  375                 380                 385

FIG. 2-3

| | | | | | | | | | | | | | | |
|---|---|---|---|---|---|---|---|---|---|---|---|---|---|---|
| tgc | caa | atg | ttt | tgt | gcc | caa | acc | gct | tgt | cca | gca | gat | tgt | gat | cct | aac | act | 1209 |
| Cys | Gln | Met | Phe | Cys 390 | Ala * | Gln | Thr | Ala | Cys | Pro 395 | Ala | Asp | Cys | Asp | Pro 400 | Asn | Thr | | caa gcc tcc tgt gag tgc ccc gaa gga tac att ctg gat gac ggc ttt att tgc    1263
Gln Ala Ser Cys Glu Cys Pro Glu Gly Tyr Ile Leu Asp Asp Gly Phe Ile Cys
        405              410              415              420 acc gat att gat gag tgt gaa aat ggt gga ttc tgt tca ggt gta tgt cac aac    1317
Thr Asp Ile Asp Glu Cys Glu Asn Gly Gly Phe Cys Ser Gly Val Cys His Asn
            425              430              435 ctg ccc ggg act ttc gaa tgt atc tgt ggt cct gac tct gca ttg gtg cga cat    1371
Leu Pro Gly Thr Phe Glu Cys Ile Cys Gly Pro Asp Ser Ala Leu Val Arg His
440              445              450              455 atc ggc act gac tgc gat tct ggg aaa gtc gat gga ggc gac tcc ggt tct gga    1425
Ile Gly Thr Asp Cys Asp Ser Gly Lys Val Asp Gly Gly Asp Ser Gly Ser Gly
        460              465              470              475 gaa cca ccc cca tct ccc act cca ggc agt act ttg acg ccc cct gct gtt gga    1479
Glu Pro Pro Pro Ser Pro Thr Pro Gly Ser Thr Leu Thr Pro Pro Ala Val Gly
        480              485              490 tta gtc cat tct ggc ttg ctc ata ggc atc tcc atc gcg agc ctg tgc ctg gtg    1533
Leu Val His Ser Gly Leu Leu Ile Gly Ile Ser Ile Ala Ser Leu Cys Leu Val
        495              500              505              510 gtg gcg ctt ttg gcg ctc ctc tgc cac ctg cgc aag aag cag ggc gcc gcc agg    1587
Val Ala Leu Leu Ala Leu Leu Cys His Leu Arg Lys Lys Gln Gly Ala Ala Arg
            515              520              525 gcc aag atg gag tac aag tgc gcg gcc cct tcc aag gag gta gtg ctg cag cac    1641
Ala Lys Met Glu Tyr Lys Cys Ala Ala Pro Ser Lys Glu Val Val Leu Gln His
530              535              540              545 gtg cgg acc gag cgg acg ccg cag aga ctc                                     1671
Val Arg Thr Glu Arg Thr Pro Gln Arg Leu
        550              555

THROMBOMODULIN VARIANTS AND USE THEREOF

REFERENCE TO RELATED APPLICATION

The present application claims the priority to U.S. Provisional Application Ser. No. 61/859,433, filed Jul. 29, 2013, which is herein incorporated by reference in its entirety.

FIELD OF THE INVENTION

The present invention relates generally to thrombomodulin, and more specifically to variants of thrombomodulin and methods of using them.

BACKGROUND OF THE INVENTION

U.S. Pat. No. 5,583,102 discloses the use of human thrombomodulin for wound healing. It teaches preparations for thrombomodulin treatment may include either a full-length recombinant human thrombomodulin protein or derivatives of full-length recombinant human thrombomodulin. The derivatives could include soluble thrombomodulin (with transmembrane, cytoplasmic and other domains deleted) or glycosylation variants of thrombomodulin (with altered O-linked oligosaccharide chains. N-linked oligosaccharide chains, or glycosaminoglycan chains). It expressly teaches that any active derivative of human thrombomodulin needs to retain the EGF-like domains 4-6 in order to bind thrombin and accelerate protein C activation.

SUMMARY OF THE INVENTION

In one aspect, the invention relates to a method of promoting wound healing, comprising: administering to a subject in need thereof a pharmaceutical composition comprising an effective amount of a mutant thrombomodulin, the mutant thrombomodulin comprising an amino acid sequence that is at least 80% identity to SEQ ID NO: 2 and having residues corresponding to $Ala^{364}$ and $Ala^{391}$ of the SEQ ID NO: 2.

In another aspect, the invention relates to a method for accelerating closure of an open wound in a diabetic. The method comprises administering to the diabetic a pharmaceutical composition comprising an effective amount of a mutant thrombomodulin, the mutant thrombomodulin comprising an amino acid sequence that is at least 80% identity to SEQ ID NO: 2 and comprising residues corresponding to $Ala^{364}$ and $Ala^{391}$ of SEQ ID NO: 2.

Further in another aspect, the invention relates to a pharmaceutical composition comprising an effective amount of a mutant thrombomodulin, the mutant thrombomodulin having the following characteristics:

(i) comprising an amino acid sequence that is at least 80% identical to SEQ ID NO: 2;
(ii) having residues corresponding to $Ala^{364}$ and $Ala^{391}$ of SEQ ID NO: 2; and
(iii) having little or no protein C activation activity.

These and other aspects will become apparent from the following description of the preferred embodiment taken in conjunction with the following drawings, although variations and modifications therein may be affected without departing from the spirit and scope of the novel concepts of the disclosure.

The accompanying drawings illustrate one or more embodiments of the invention and, together with the written description, serve to explain the principles of the invention. Wherever possible, the same reference numbers are used throughout the drawings to refer to the same or like elements of an embodiment.

BRIEF DESCRIPTION OF THE DRAWINGS

FIGS. 1-1 to 1-3 show a wild-type human thrombomodulin nucleotide (SEQ ID NO: 6) and amino acid sequences (SEQ ID NO: 5).

FIGS. 2-1 to 2-3 show mutant thrombomodulin (TMD123NA) nucleotide (SEQ ID NO: 3) and amino acid sequences (SEQ ID NO: 2).

DETAILED DESCRIPTION OF THE INVENTION

The present invention is more particularly described in the following examples that are intended as illustrative only since numerous modifications and variations therein will be apparent to those skilled in the art. Various embodiments of the invention are now described in detail. Referring to the drawings, like numbers indicate like components throughout the views. As used in the description herein and throughout the claims that follow, the meaning of "a", "an", and "the" includes plural reference unless the context clearly dictates otherwise. Also, as used in the description herein and throughout the claims that follow, the meaning of "in" includes "in" and "on" unless the context clearly dictates otherwise. Moreover, titles or subtitles may be used in the specification fix the convenience of a reader, which shall have no influence on the scope of the present invention. Additionally, some terms used in this specification are more specifically defined below.

DEFINITIONS

The terms used in this specification generally have their ordinary meanings in the art, within the context of the invention, and in the specific context where each term is used. Certain terms that are used to describe the invention are discussed below, or elsewhere in the specification, to provide additional guidance to the practitioner regarding the description of the invention. For convenience, certain terms may be highlighted, for example using italics and/or quotation marks. The use of highlighting has no influence on the scope and meaning of a term; the scope and meaning of a term is the same, in the same context, whether or not it is highlighted. It will be appreciated that same thing can be said in more than one way. Consequently, alternative language and non ms may be used for any one or more of the terms discussed herein, nor is any special significance to be placed upon whether or not a term is elaborated or discussed herein. Synonyms for certain terms are provided. A recital of one or more synonyms does not exclude the use of other synonyms. The use of examples anywhere in this specification including examples of any terms discussed herein is illustrative only, and in no way limits the scope and meaning of the invention or of any exemplified term. Likewise, the invention is not limited to various embodiments given in this specification.

Unless otherwise defined, all technical and scientific terms used herein have the same meaning as commonly understood by one of ordinary skill in the art to which this invention pertains. In the case of conflict, the present document, including definitions will control.

As used herein, "around", "about" or "approximately" shall generally mean within 20 percent, preferably within 10 percent, and more preferably within 5 percent of a given value or range. Numerical quantities given herein are approximate, meaning that the term "around", "about" or "approximately" can be inferred if not expressly stated.

As used herein, when a number or a range is recited, ordinary skill in the art understand it intends to encompass an appropriate, reasonable range for the particular field related to the invention.

By less than 20%, it meant that all hundredth and tenth unit amounts within the range are specifically disclosed as part of the invention. Thus, less than 19%, 18%, 17%, 16%, 15%, 14%, . . . 3%, 2%, and 1% unit amounts are included as embodiments of this invention.

By less than 5%, it meant that all hundredth and tenth unit amounts within the range are specifically disclosed as part of the invention. Thus, less than 4%, 3%, 2%, or 1% unit amounts are included as embodiments of this invention.

"Wounds" can be characterized as open wounds and closed wounds. Open wounds can be classified into a number of different types, including incisions (caused by a clean, sharp-edged object such as a knife or a razor), lacerations (rough, irregular wounds caused by crushing or ripping, forces), abrasions or grazes (a superficial wound in which the topmost layers of the skin are scraped off, often caused by a sliding, fall onto a rough surface), and puncture wounds (caused by an object puncturing the skin, such as a nail or needle). Closed wounds have far fewer categories, but are just as dangerous as open wounds. They are contusions or bruise (caused by blunt force trauma that damages tissues under the skin), hematoma (caused by damage to a blood vessel that in turn causes blood to collect under the skin) and crushing injuries (caused by a great or extreme amount of force applied over a long period of time).

SEQ ID NO: 1 (mutant rTMD23NA): protein sequence, 274 aa; 141A, 168A, without domain 1; Asparagine (Asn) at 364 and 391 of wild type of TMD 123 were mutated to Alanine (Ala).

SEQ ID NO: 2 (mutant rTMD123NA): protein sequence (557 aa, 364A, 391A); without signal peptide sequence.

SEQ ID NO: 3 (mutant rTMD123NA): DNA sequence (1671 nt) encoding SEQ ID NO: 2, without signal peptide sequence.

SEQ ID NO: 4 (wild-type rTMD23): protein sequence of wild-type TMD23 (274 aa); containing domains 2 (224Ala~462Cys) and 3 (Asp463~Ser 497 of thrombomodulin TMD123, SEQ ID NO: 5, without signal peptide sequence).

SEQ ID NO: 5 (wild-type rTMD123): protein sequence (557 aa; 364N, 391N), without a signal peptide sequence. Domain 1, 1Ala~223Gly; Domain 2, 224Ala~462Cys; Domain 3, 463Asp~497Ser.

SEQ ID NO: 6 (wild-type rTMD123): DNA sequence (1671 nt), without a signal peptide sequence.

In one aspect, the invention relates to a method of promoting wound healing, comprising: administering to a subject in need thereof a pharmaceutical composition comprising an effective amount of a mutant thrombomodulin, the mutant thrombomodulin comprising an amino acid sequence that is at least 80% identity to SEQ ID NO: 2 and having residues corresponding to Ala$^{364}$ and Ala$^{391}$ of the SEQ ID NO: 2.

In one embodiment of the invention, the mutant thrombomodulin has little or no protein C activation activity.

In another embodiment of the invention, the mutant thrombomodulin is a recombinant human thrombomodulin mutant without glycosylation at the residues corresponding to Ala$^{364}$ and Ala$^{391}$ of SEQ ID NO: 2.

In another embodiment of the invention, the mutant thrombomodulin is least 90% identical to the amino acid sequence of SEQ ID No: 2.

In another embodiment of the invention, the polypeptide is administered at a wound site.

In another embodiment of the invention, the composition is in gel, cream, paste, lotion, spray, suspension, solution, dispersion salve, hydrogel or ointment form.

In another embodiment of the invention, the composition is administered to the subject topically, or via injection:

In another embodiment of the invention, the composition is in solution or gel form.

In another embodiment of the invention, the wound is an open wound resulted from an incision, a laceration, an abrasion, a puncture wound, a blister, a skin tear, a donor or graft site, acne, a hematoma, a crushing injury, an injury caused by dermabrasion, or an injury caused by laser resurfacing.

In another embodiment of the invention, the wound comprises a diabetic foot ulcer.

In another aspect, the invention relates to a method for accelerating closure of an open wound in a diabetic. The method comprises administering to the diabetic a pharmaceutical composition comprising an effective amount of a mutant thrombomodulin, the mutant thrombomodulin comprising an amino acid sequence that is at least 80% identity to SEQ ID NO: 2 and comprising residues corresponding to Ala$^{364}$ and Ala$^{391}$ of SEQ ID NO: 2.

Further in another aspect, the invention relates to a pharmaceutical composition comprising an effective amount of a mutant thrombomodulin, the mutant thrombomodulin having the following characteristics:
  (i) comprising an amino acid sequence that is at least 80% identical to SEQ ID NO: 2;
  (ii) having residues corresponding to Ala$^{364}$ and Ala$^{391}$ of SEQ ID NO: 2; and
  (iii) having little or no protein C activation activity.

In another embodiment of the invention, the mutant thrombomodulin is free of domain 1 of a wild-type thrombomodulin.

In another embodiment of the invention, the amino acid sequence of the mutant thrombomodulin is SEQ ID NO: 1. Alternatively, the amino acid sequence of the mutant thrombomodulin consists of SEQ ID NO: 1.

In another embodiment of the invention, the mutant thrombomodulin is a recombinant human thrombomodulin mutant without glycosylation at the residues corresponding to Ala$^{364}$ and Ala$^{391}$ of SEQ ID NO: 2.

In another embodiment of the invention, the mutant thrombomodulin is at least 90% identical to the amino acid sequence of SEQ ID NO: 2.

In another embodiment of the invention, the mutant thrombomodulin contains less than 15% of mannose of, and less than 5% of glucosamine of, wild-type thrombomodulin.

EXAMPLES

Without intent to limit the scope of the invention, exemplary instruments, apparatus, methods and their related results according to the embodiments of the present invention are given below. Note that titles or subtitles may be used in the examples for convenience of a reader, which in no way should limit the scope of the invention. Moreover, certain theories are proposed and disclosed herein; however, in no way they, whether they are right or wrong, should limit the scope of the invention so long as the invention is practiced according to the invention without regard for any particular theory or scheme of action.

Materials and Methods

Preparation of rTMD23. pPICZ A vector (invitrogen Corp) was used for expression and secretion of recombinant human TMD23 in *Pichia pastoris* protein expression system. Briefly, a DNA fragment coding for TMD23 (residues Ala224~Ser497 of SEQ ID NO: 2) were obtained by a polymerase chain reaction of human umbilical vein endothelial cell (HUVEC) cDNA. The fermentation medium containing expressed TMD23 was applied to a nickel-chelating Sepharose column (Amersham Pharmacia Biotech AB), and TMD23-containing fractions were eluted with imidazole.

Preparation of rTMD23NA. Using recombinant DNA technology, a *Pichia* strain has been developed to produce TMD23. Based on the original human thrombomodulin domain 2 and domain 3 sequence, a synthetic DNA was generated according to the preferred codon utilization by yeast (codon optimization) to enhance the efficiency of the t-RNA utilization. This codon-optimized TMD23 gene was then subcloned to the expression vector pPICZαA. In addition, using site-directed mutagenesis, two potential N-linked glycosylation sites (N364, N391 of SEQ ID NO: 5) on TMD23 sequence were changed to alanine. The TMD23NA-containing vector was transfected to *Pichia pastoris* X-33 by electroporation. The Fermentation medium containing expressed TMD23NA was applied to Hydrophobic, lion-Exchanged, and Size-Exclusion Chromatography column, and TMD23NA-containing fractions were eluted with buffer.

Animals. Non-insulin dependent diabetic mellitus (NIDDM) male mice (C577BLKS/J Iar-+Leprdb/+Leprdb), weighing 50±5 g (~10 weeks of age), provided by institute for Animal Reproduction (IAR, Japan) were used. These animals exhibited hyperinsulinemia, hyperglycemia and islet atrophy and were used at about 12-13 weeks of age. The animals were housed in Individually Ventilated Cages Racks (IVC Racks, 36 Mini isolator systems) under a Specific Pathogen-Free (SPF) condition throughout the experiment. Each animal cage (in cm, 26.7 length×20.7 width×14.0 height) was sterilized with autoclave and contained 1 mouse, and the animals were then maintained in a hygienic environment under controlled temperature (20-24° C.) and humidity (40%-70%) with 12-hour light/dark cycle. The animals were given a free access to sterilized lab chow and sterilized distilled water ad libitum. All aspects of this work, i. e. housing, experimentation and disposal of animals, were performed in general accordance with the Guide for the Care and Use of Laboratory Animals (National Academy Press, Washington, D. C., 2011).

Thrombomodulin Activity Assay—rTMD23 and rTMD23NA were split into wells of a 96-well plate and allowed to coat overnight. The plate was washed in a buffer containing 20 mM Tris (pH 7.4), 0.15 M NaCl, 2.5 mM $CaCl_2$, and 5 mg/ml bovine serum albumin and incubated with a reaction mixture (37.5 nM thrombin and 5 µg/ml protein C in a washing buffer) at 37° C. for 30 min. Protein C activation was terminated by adding 40 µl of antithrombin III (6 IU/ml) and heparin (12 IU/ml). The enzymatic activity of activated protein C was measured with the peptide substrate H-D-Lys-Z-Pro-Arg-4-nitroanilidediacetate (Chromozym PCa; 0.5 mM in 20 mM Tris, pH 7.4, 0.15 M NaCl, and 5 mg/ml bovine serum albumin) at 37° C. The absorbance change at 405 nm was measured with a SUNRISE™ Microplate Reader (TECAN Austria GmbH, Gröig, Austria). Controls containing thrombin and protein C in the absence of thrombomodulin were treated similarly.

It was discovered that the mutant thrombomodulin has no or little protein C activation activity.

db/db Mice Wound Healing Assay Methods—Groups of 5 C57BLKS/J Iar-+Leprdb/+Leprdb male mice weighing 50±5 g were used (~13 weeks of age) in this study. Tested mice were grouped base on the Day 0 pre-treated blood glucose levels. During the testing period, the animals were individually housed in Individually Ventilated Cages Racks (IVC Racks, 36 Mini Isolator Systems). Under isoflurane anesthesia, the shoulder and back region of each animal was shaved. A sharp punch (ID 12 mm) was used to remove the skin including panniculus carnosus and adherent tissues. The wound area, traced onto the clear plastic sheets on days 1, 3, 5, 7, 9, 11, 13 and 15, were quantified by using an image-ProPlus (Media Cybernetics, Version 4.5.0.29). Test compounds and vehicle were applied topically following the injury and once daily thereafter for a total of 14 consecutive days, whereas CGS-21680, a reference compound, in 0.5% CMC/PBS (pH 7.4, 20 µL/mouse) was administered in the same dosing pattern as the test substance. The wound half-closure time (CT50) was determined and one-way ANOVA followed by Dunnett's test was applied for a comparison between the treated and the vehicle groups at each measurement time point. Differences were considered statistical significance at $P<0.05$.

Results

Figure 3:
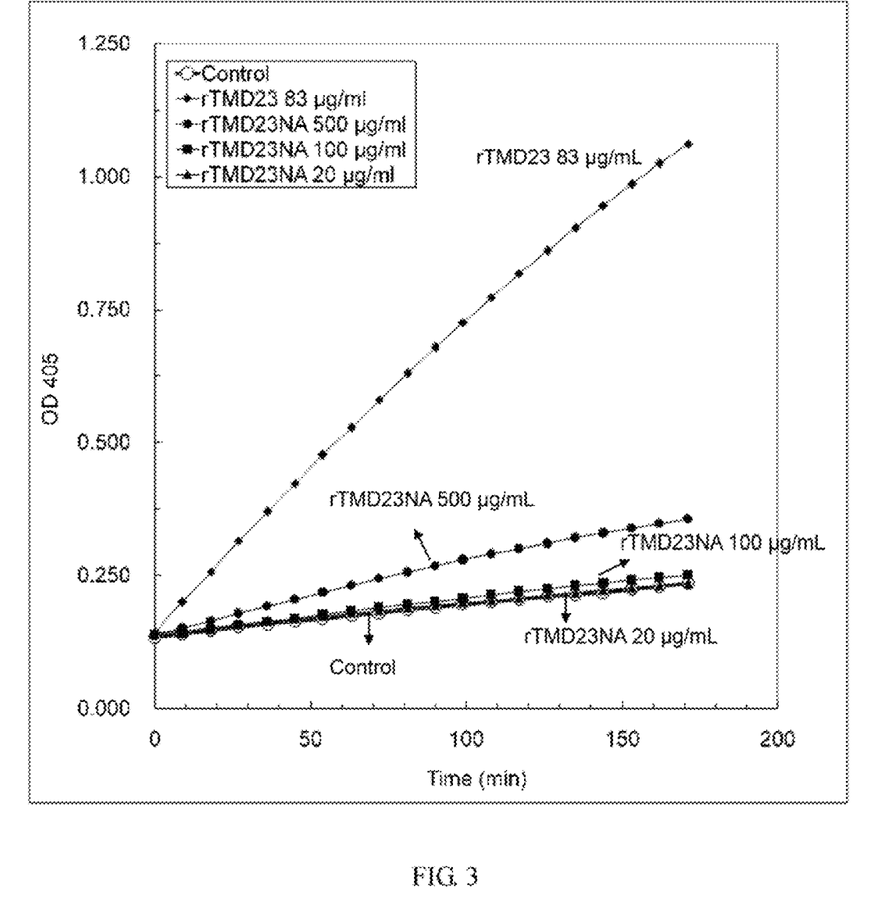
FIG. 3 shows thrombin-dependent activation of protein C in the presence of recombinant TMD23 and its mutants rTMD23NA.

The nucleotide and amino acid sequences of thrombomodulin (SEQ ID NOs: 6 and 5) and its mutant (SEQ ID NOs: 3 and 2) without the signal peptide sequence are shown in FIGS. 1 and 2, respectively. FIG. 3 shows thrombin-dependent activation of protein C in the presence of recombinant TMD23 and its mutants. The generation of activated protein C by thrombin in complex with TMD23 or its mutant protein was measured by monitoring the hydrolysis of a specific protein C substrate, Chromozyme PCa, with optical absorption at 405 nm. The data showed that only recombinant TMD23 gave rise to thrombin-dependent protein C activation. The mutant rTMD23NA lost its cofactor activity in catalyzing thrombin-dependent activation of Protein C. The mutant rTMD23NA was generated as follows: two putative N-linked glycosylation sites in the sequence of human TM at N382 and N409 (referring to wild-type with a signal peptide from a.a. 1-a.a. 18) were identified and mutated to Ala.

Figure 4:
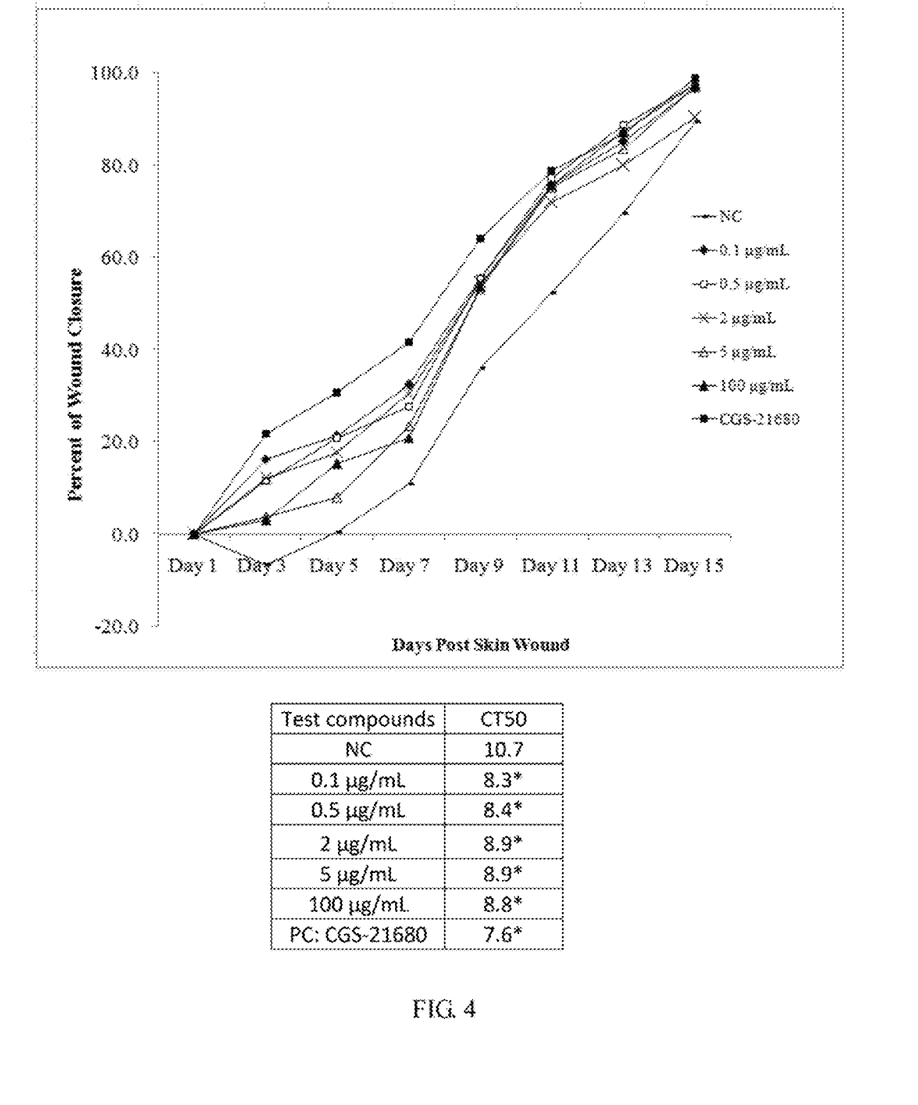
FIG. 4 shows time course of wound closure in diabetic mice (Lepr db) treated with rTMD23NA via topical application.

The mutant thrombomodulin rTMD23NA according to the invention showed a wound-healing effect even though having little protein C activation activity. FIG. 4 shows a time course of wound closure in diabetic mice (Lepr db) treated with rTMD23NA via a topical application. The rTMD23NA or control vehicle was administered topically once daily for 14 consecutive days. The wound area, traced onto clear plastic sheets on day 1, 3, 5, 7, 9, 11, 13 and 15, was measured by using an image-analyzer.

Figure 5:
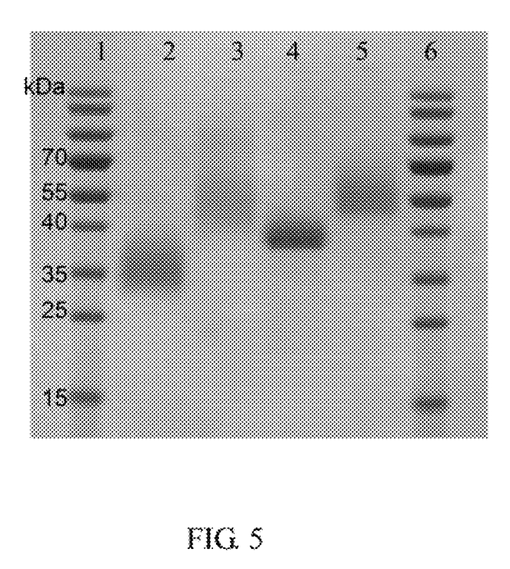
FIG. 5 is a photograph showing the results of SDS-PAGE.
Figure 11:
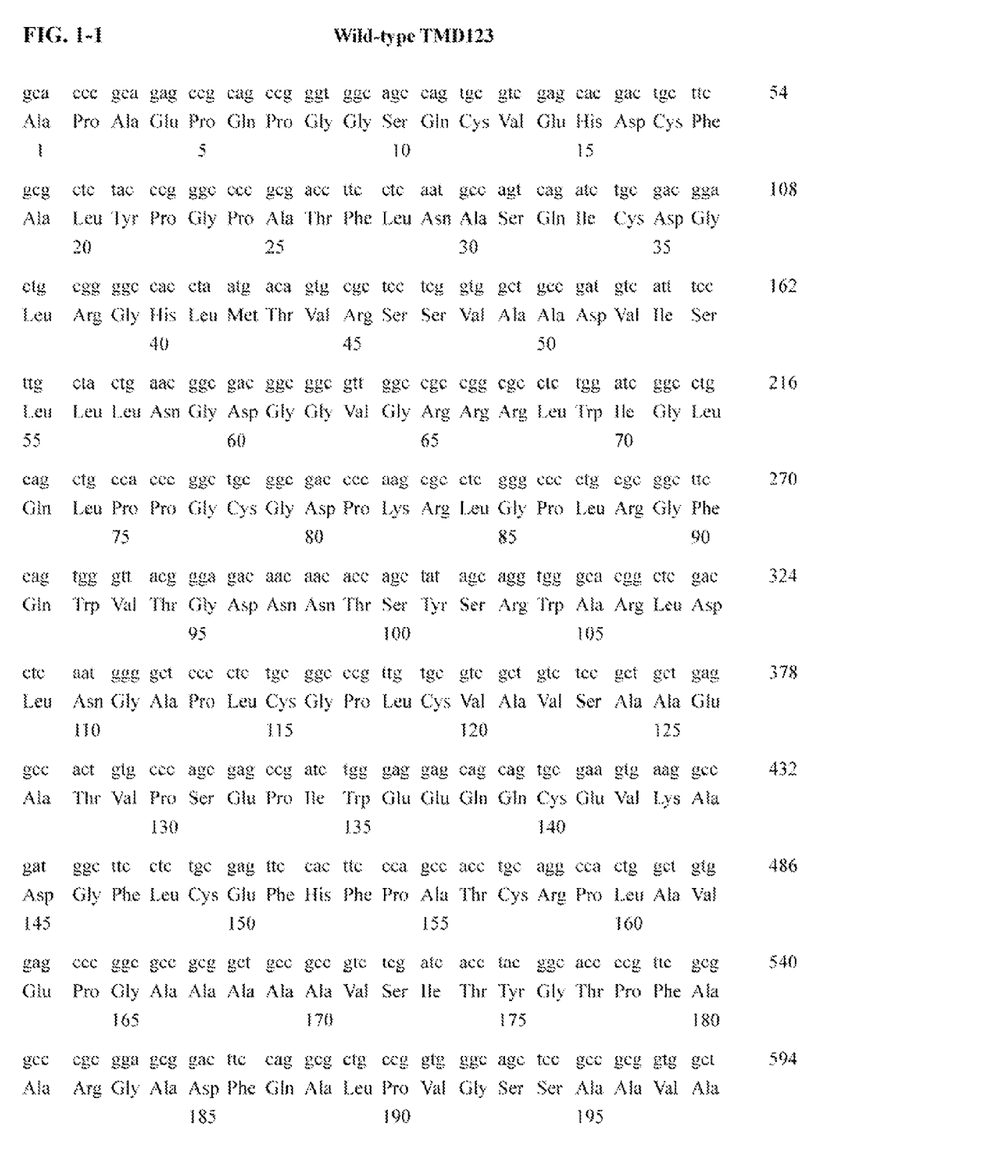
Figure 21:
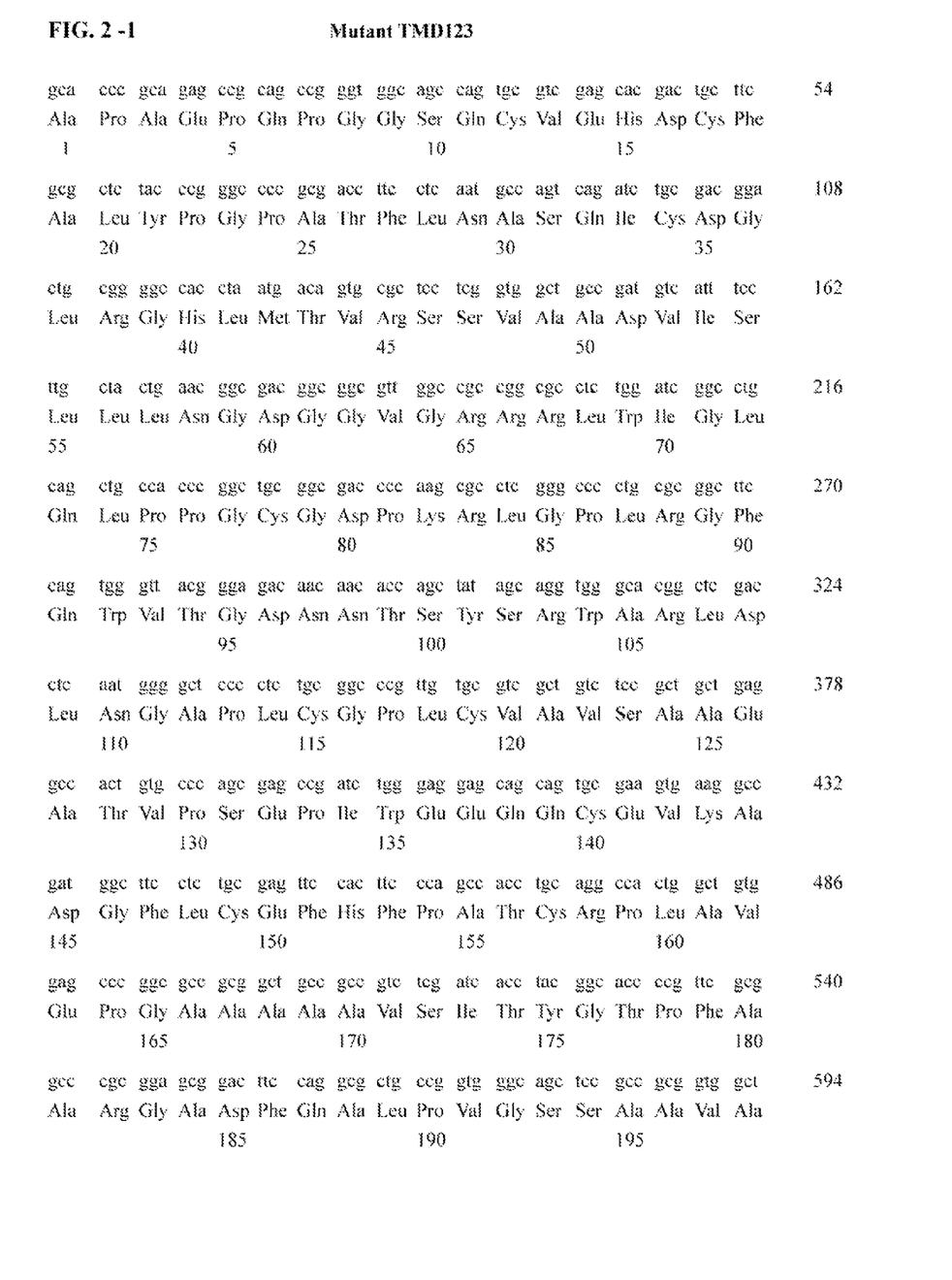
Figure 23:
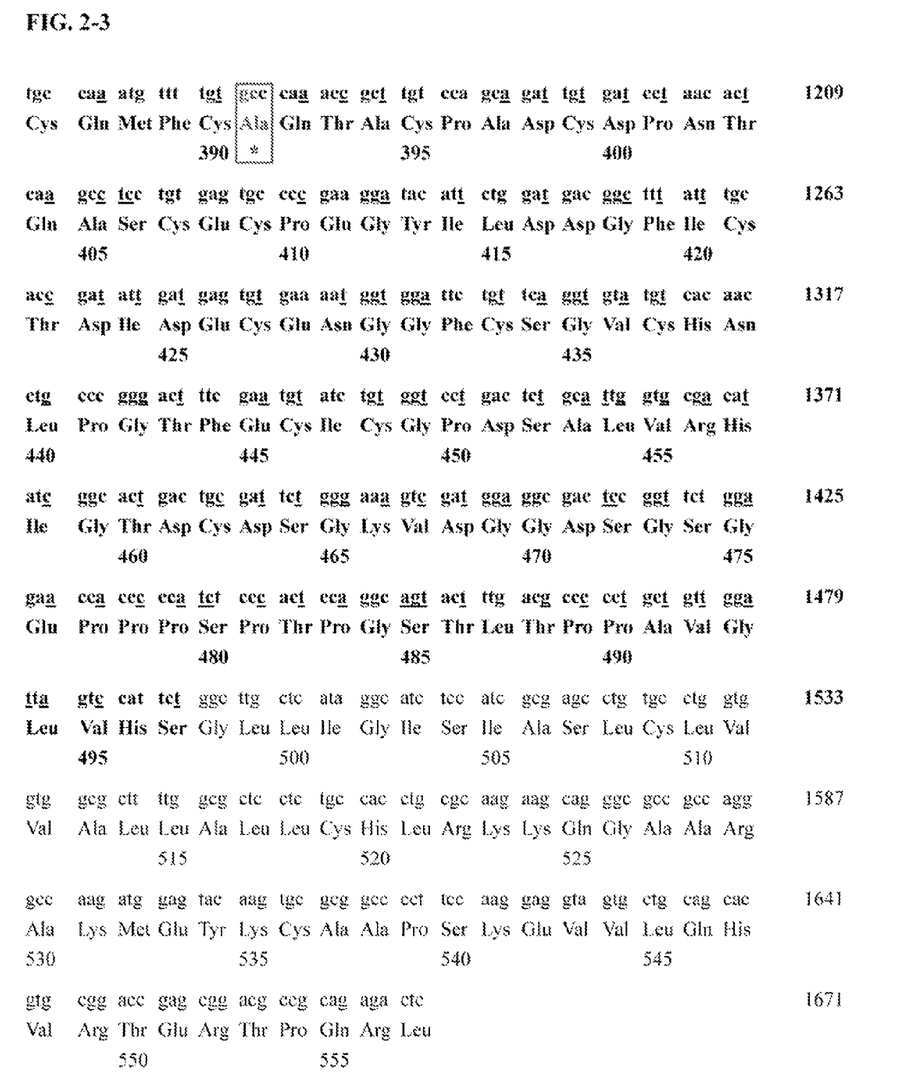

The wild-type TMD23 protein contained multiple sugars and was difficult to be purified. The separated pattern of TMD23 by SDS-PAGE was smearing. To solve this problem, two putative N-glycosylation Asn residues, N364 and N391 (referring to SEQ ID NO: 5) of TMD23, were mutated to Ala by a site-directed mutagenesis technique. Afterward, the separated pattern of the mutant TMD 23NA by SDS-PAGE was clear and easy to be purified (FIG. 5). Gel information: 12% Bis-Tris gel (SDS-PAGE) Invitrogen NP0341BOX) Buffer Information: NUPAGE MOPS BISTRIS BFR (Invitrogen KIT NP0050). EP Condition: 150 Volt 70 min. Lane 1. PageRuler Prestained Protein Ladder (Thermo 266161); Lane 2: Non-reduced Form of rTMD23NA (CY-F04-P01

Batch); Lane 3: Non-reduced Form of rTMD23; Lane 4: Reduced Form of rTMD23NA (CY-F04-P01 Batch); Lane 5: Reduced Form of rTMD23; Lane 6: PageRuler Prestained Protein Ladder (Thermo 26616).

The monosaccharide contents of wild type and mutant TMD23 were analyzed. Per mg wild type rTMD23 contained 1688 nmole mannose and 107.7 nmole glucosamine. After mutation, per mg mutant rTMD23NA contained 263.1 nmole mannose and 1.23 nmole glucosamine. In other words, the mutant rTMD23NA contained 15% of mannose and 1% of glucosamine of wild-type TMD23.

The foregoing description of the exemplary embodiments of the invention has been presented only for the purposes of illustration and description and is not intended to be exhaustive or to limit the invention to the precise forms disclosed. Many modifications and variations are possible in light of the above teaching.

The embodiments and examples were chosen and described in order to explain the principles of the invention and their practical application so as to enable others skilled in the art to utilize the invention and various embodiments and with various modifications as are suited to the particular use contemplated. Alternative embodiments will become apparent to those skilled in the art to which the present invention pertains without departing from its spirit and scope. Accordingly, the scope of the present invention is defined by the appended claims rather than the foregoing description and the exemplary embodiments described therein.

Some references, which may include patents, patent applications and various publications, are cited and discussed in the description of this invention. The citation and/or discussion of such references is provided merely to clarify the description of the present invention and is not an admission that any such reference is "prior art" to the invention described herein. All references cited and discussed in this specification are incorporated herein by reference in their entireties and to the same extent as if each reference was individually incorporated by reference.

What is claimed is:

1. A method of promoting wound healing, comprising: administering to a subject in need thereof a pharmaceutical composition comprising an effective amount of a mutant thrombomodulin, the mutant thrombomodulin comprising an amino acid sequence that is at least 80% identical to SEQ ID NO: 2 and having residues corresponding to $Ala^{364}$ and $Ala^{391}$ of the SEQ ID NO: 2.

2. The method of claim 1, wherein the mutant thrombomodulin demonstrates reduced protein C activation activity as compared to the thrombomodulin represented by SEQ ID NO:4.

3. The method of claim 1, wherein the mutant thrombomodulin is a recombinant human thrombomodulin mutant that has no glycosylation at the residues corresponding to $Ala^{364}$ and $Ala^{391}$ of SEQ ID NO: 2.

4. The method of claim 1, wherein the amino acid sequence of the mutant thrombomodulin is SEQ ID NO: 1.

5. The method of claim 1, wherein the mutant thrombomodulin lacks the domain 1 of a wild-type human thrombomodulin.

6. The method of claim 1, wherein the mutant thrombomodulin is least 90% identical to the amino acid sequence of SEQ ID NO: 2.

7. The method of claim 1, wherein the mutant thrombomodulin is administered at a wound site.

8. The method of claim 1, wherein the composition is in gel, cream, paste, lotion, spray, suspension, solution, dispersion salve, hydrogel or ointment form.

9. The method of claim 1, wherein the composition is administered to the subject topically, or via injection.

10. The method of claim 1, wherein the amino acid sequence of the mutant thrombomodulin consists essentially of SEQ ID NO: 1 or SEQ ID NO 2.

11. The method of claim 1, wherein the wound is an open wound resulting from an incision, a laceration, an abrasion, a puncture wound, a blister, a skin tear, a donor or graft site, acne, a hematoma, a crushing injury, an injury caused by dermabrasion, or an injury caused by laser resurfacing.

12. The method of claim 1, wherein the wound is a diabetic foot ulcer.

13. The method of claim 1, wherein the wound is in a subcutaneous tissue.

14. A method for accelerating closure of an open wound in a diabetic, comprising: administering to the diabetic a pharmaceutical composition comprising an effective amount of a mutant thrombomodulin, the mutant thrombomodulin comprising an amino acid sequence that is at least 80% identity to SEQ ID NO: 2 and comprising residues corresponding to $Ala^{364}$ and $Ala^{391}$ of SEQ ID NO: 2.

15. The method of claim 14, wherein the wound comprises a diabetic foot ulcer.

16. The method of claim 14, wherein the mutant thrombomodulin lacks domain 1 of a wild-type human thrombomodulin.

17. A pharmaceutical composition comprising an effective amount of a mutant thrombomodulin, the mutant thrombomodulin exhibiting the following characteristics:
   (i) comprising an amino acid sequence that is at least 80% identical to SEQ ID NO: 2;
   (ii) having residues corresponding to $Ala^{364}$ and $Ala^{391}$ of SEQ ID NO: 2; and
   (iii) demonstrates reduced protein C activation activity as compared to the thrombomodulin represented by SEQ ID NO:4.

18. The pharmaceutical composition of claim 17, wherein the amino acid sequence of the mutant thrombomodulin comprises SEQ ID NO: 1.

19. The pharmaceutical composition of claim 18, wherein the mutant thrombomodulin lacks domain 1 of wild-type thrombomodulin.

20. The pharmaceutical composition of claim 17, wherein the mutant thrombomodulin contains less mannose and glucosamine monosaccharides than wild-type thrombomodulin.

* * * * *

SEQUENCE LISTING

```
<160> NUMBER OF SEQ ID NOS: 6

<210> SEQ ID NO 1
<211> LENGTH: 274
<212> TYPE: PRT
<213> ORGANISM: Homo sapiens

<400> SEQUENCE: 1

Ala Trp Asp Cys Ser Val Glu Asn Gly Gly Cys Glu His Ala Cys Asn
1               5                   10                  15

Ala Ile Pro Gly Ala Pro Arg Cys Gln Cys Pro Ala Gly Ala Ala Leu
            20                  25                  30

Gln Ala Asp Gly Arg Ser Cys Thr Ala Ser Ala Thr Gln Ser Cys Asn
        35                  40                  45

Asp Leu Cys Glu His Phe Cys Val Pro Asn Pro Asp Gln Pro Gly Ser
    50                  55                  60

Tyr Ser Cys Met Cys Glu Thr Gly Tyr Arg Leu Ala Ala Asp Gln His
65                  70                  75                  80

Arg Cys Glu Asp Val Asp Asp Cys Ile Leu Glu Pro Ser Pro Cys Pro
                85                  90                  95

Gln Arg Cys Val Asn Thr Gln Gly Gly Phe Glu Cys His Cys Tyr Pro
            100                 105                 110

Asn Tyr Asp Leu Val Asp Gly Glu Cys Val Glu Pro Val Asp Pro Cys
        115                 120                 125

Phe Arg Ala Asn Cys Glu Tyr Gln Cys Gln Pro Leu Ala Gln Thr Ser
    130                 135                 140

Tyr Leu Cys Val Cys Ala Glu Gly Phe Ala Pro Ile Pro His Glu Pro
145                 150                 155                 160

His Arg Cys Gln Met Phe Cys Ala Gln Thr Ala Cys Pro Ala Asp Cys
                165                 170                 175

Asp Pro Asn Thr Gln Ala Ser Cys Glu Cys Pro Glu Gly Tyr Ile Leu
            180                 185                 190

Asp Asp Gly Phe Ile Cys Thr Asp Ile Asp Glu Cys Glu Asn Gly Gly
        195                 200                 205

Phe Cys Ser Gly Val Cys His Asn Leu Pro Gly Thr Phe Glu Cys Ile
    210                 215                 220

Cys Gly Pro Asp Ser Ala Leu Val Arg His Ile Gly Thr Asp Cys Asp
225                 230                 235                 240
```

```
Ser Gly Lys Val Asp Gly Gly Asp Ser Gly Ser Gly Glu Pro Pro Pro
            245                 250                 255

Ser Pro Thr Pro Gly Ser Thr Leu Thr Pro Pro Ala Val Gly Leu Val
            260                 265                 270

His Ser

<210> SEQ ID NO 2
<211> LENGTH: 557
<212> TYPE: PRT
<213> ORGANISM: Homo sapiens

<400> SEQUENCE: 2

Ala Pro Ala Glu Pro Gln Pro Gly Gly Ser Gln Cys Val Glu His Asp
1               5                   10                  15

Cys Phe Ala Leu Tyr Pro Gly Pro Ala Thr Phe Leu Asn Ala Ser Gln
            20                  25                  30

Ile Cys Asp Gly Leu Arg Gly His Leu Met Thr Val Arg Ser Ser Val
        35                  40                  45

Ala Ala Asp Val Ile Ser Leu Leu Leu Asn Gly Asp Gly Gly Val Gly
    50                  55                  60

Arg Arg Arg Leu Trp Ile Gly Leu Gln Leu Pro Pro Gly Cys Gly Asp
65                  70                  75                  80

Pro Lys Arg Leu Gly Pro Leu Arg Gly Phe Gln Trp Val Thr Gly Asp
                85                  90                  95

Asn Asn Thr Ser Tyr Ser Arg Trp Ala Arg Leu Asp Leu Asn Gly Ala
            100                 105                 110

Pro Leu Cys Gly Pro Leu Cys Val Ala Val Ser Ala Ala Glu Ala Thr
        115                 120                 125

Val Pro Ser Glu Pro Ile Trp Glu Glu Gln Gln Cys Glu Val Lys Ala
    130                 135                 140

Asp Gly Phe Leu Cys Glu Phe His Phe Pro Ala Thr Cys Arg Pro Leu
145                 150                 155                 160

Ala Val Glu Pro Gly Ala Ala Ala Ala Val Ser Ile Thr Tyr Gly
                165                 170                 175

Thr Pro Phe Ala Ala Arg Gly Ala Asp Phe Gln Ala Leu Pro Val Gly
            180                 185                 190

Ser Ser Ala Ala Val Ala Pro Leu Gly Leu Gln Leu Met Cys Thr Ala
        195                 200                 205

Pro Pro Gly Ala Val Gln Gly His Trp Ala Arg Glu Ala Pro Gly Ala
    210                 215                 220

Trp Asp Cys Ser Val Glu Asn Gly Gly Cys Glu His Ala Cys Asn Ala
225                 230                 235                 240

Ile Pro Gly Ala Pro Arg Cys Gln Cys Pro Ala Gly Ala Ala Leu Gln
                245                 250                 255

Ala Asp Gly Arg Ser Cys Thr Ala Ser Ala Thr Gln Ser Cys Asn Asp
            260                 265                 270

Leu Cys Glu His Phe Cys Val Pro Asn Pro Asp Gln Pro Gly Ser Tyr
        275                 280                 285

Ser Cys Met Cys Glu Thr Gly Tyr Arg Leu Ala Ala Asp Gln His Arg
    290                 295                 300

Cys Glu Asp Val Asp Asp Cys Ile Leu Glu Pro Ser Pro Cys Pro Gln
305                 310                 315                 320

Arg Cys Val Asn Thr Gln Gly Gly Phe Glu Cys His Cys Tyr Pro Asn
                325                 330                 335
```

```
Tyr Asp Leu Val Asp Gly Glu Cys Val Glu Pro Val Asp Pro Cys Phe
                340                 345                 350
Arg Ala Asn Cys Glu Tyr Gln Cys Gln Pro Leu Ala Gln Thr Ser Tyr
            355                 360                 365
Leu Cys Val Cys Ala Glu Gly Phe Ala Pro Ile Pro His Glu Pro His
    370                 375                 380
Arg Cys Gln Met Phe Cys Ala Gln Thr Ala Cys Pro Ala Asp Cys Asp
385                 390                 395                 400
Pro Asn Thr Gln Ala Ser Cys Glu Cys Pro Glu Gly Tyr Ile Leu Asp
                405                 410                 415
Asp Gly Phe Ile Cys Thr Asp Ile Asp Glu Cys Glu Asn Gly Gly Phe
            420                 425                 430
Cys Ser Gly Val Cys His Asn Leu Pro Gly Thr Phe Glu Cys Ile Cys
    435                 440                 445
Gly Pro Asp Ser Ala Leu Val Arg His Ile Gly Thr Asp Cys Asp Ser
                455                 460
    450
Gly Lys Val Asp Gly Gly Asp Ser Gly Ser Gly Glu Pro Pro Pro Ser
465                 470                 475                 480
Pro Thr Pro Gly Ser Thr Leu Thr Pro Pro Ala Val Gly Leu Val His
                485                 490                 495
Ser Gly Leu Leu Ile Gly Ile Ser Ile Ala Ser Leu Cys Leu Val Val
            500                 505                 510
Ala Leu Leu Ala Leu Leu Cys His Leu Arg Lys Lys Gln Gly Ala Ala
    515                 520                 525
Arg Ala Lys Met Glu Tyr Lys Cys Ala Ala Pro Ser Lys Glu Val Val
    530                 535                 540
Leu Gln His Val Arg Thr Glu Arg Thr Pro Gln Arg Leu
545                 550                 555

<210> SEQ ID NO 3
<211> LENGTH: 1671
<212> TYPE: DNA
<213> ORGANISM: Homo sapiens

<400> SEQUENCE: 3
gcacccgcag agccgcagcc gggtggcagc cagtgcgtcg agcacgactg cttcgcgctc      60
tacccgggcc ccgcgacctt cctcaatgcc agtcagatct gcgacggact gcggggccac     120
ctaatgacag tgcgctcctc ggtggctgcc gatgtcattt ccttgctact gaacggcgac     180
ggcggcgttg ccgccggcg cctctggatc ggcctgcagc tgccacccgg ctgcggcgac     240
cccaagcgcc tcgggcccct gcgcggcttc cagtgggtta cgggagacaa caacaccagc     300
tatagcaggt gggcacggct cgacctcaat ggggctcccc tctgcggccc gttgtgcgtc     360
gctgtctccg ctgctgaggc cactgtgccc agcgagccga tctgggagga gcagcagtgc     420
gaagtgaagg ccgatggctt cctctgcgag ttccacttcc agccacctg caggccactg     480 gctgtggagc ccggcgccgc ggctgccgcc gtctcgatca cctacggcac ccgttcgcg     540 gcccgcggag cggacttcca ggcgctgccg gtgggcagct ccgccgcggt ggctcccctc     600
ggcttacagc taatgtgcac cgcgccgccc ggagcggtcc aggggcactg gccagggag     660 gcgccgggcg catgggactg ctcagtggaa aacggaggtt gcgaacatgc atgtaacgcc     720
atccctggtg cccaagatg tcaatgccca gctggggctg cactgcaagc agatggcaga     780
tcttgtactg cttccgctac acaatcttgt aacgatttgt gtgaacattt ttgtgttcca     840
```

-continued

| | |
|---|---|
| aatccagacc aacctggttc ttactcttgc atgtgtgaaa cgggttacag attggctgcc | 900 |
| gaccaacata gatgtgagga tgttgatgat tgtatattgg aacctagtcc atgtcctcaa | 960 |
| agatgcgtca acactcaagg tgggttcgaa tgccattgct accccaatta tgatctggtt | 1020 |
| gacggtgagt gtgtagagcc agtcgatcct tgtttccgag ccaactgtga gtaccaatgt | 1080 |
| cagcctttgg ctcaaactag ttacctgtgt gtctgtgcag agggtttcgc tcctattcct | 1140 |
| cacgaacccc acagatgcca aatgttttgt gcccaaaccg cttgtccagc agattgtgat | 1200 |
| cctaacactc aagcctcctg tgagtgcccc gaaggataca ttctggatga cggctttatt | 1260 |
| tgcaccgata ttgatgagtg tgaaaatggt ggattctgtt caggtgtatg tcacaacctg | 1320 |
| cccgggactt tcgaatgtat ctgtggtcct gactctgcat tggtgcgaca tatcggcact | 1380 |
| gactgcgatt ctgggaaagt cgatggaggc gactccggtt ctggagaacc accccatct | 1440 |
| cccactccag gcagtacttt gacgccccct gctgttggat tagtccattc tggcttgctc | 1500 |
| ataggcatct ccatcgcgag cctgtgcctg gtggtggcgc ttttggcgct cctctgccac | 1560 |
| ctgcgcaaga agcagggcgc cgccaggggcc aagatggagt acaagtgcgc ggccccttcc | 1620 |
| aaggaggtag tgctgcagca cgtgcggacc gagcggacgc cgcagagact c | 1671 |

<210> SEQ ID NO 4
<211> LENGTH: 274
<212> TYPE: PRT
<213> ORGANISM: Homo sapiens

<400> SEQUENCE: 4

Ala Trp Asp Cys Ser Val Glu Asn Gly Gly Cys Glu His Ala Cys Asn
1               5                   10                  15

Ala Ile Pro Gly Ala Pro Arg Cys Gln Cys Pro Ala Gly Ala Ala Leu
            20                  25                  30

Gln Ala Asp Gly Arg Ser Cys Thr Ala Ser Ala Thr Gln Ser Cys Asn
        35                  40                  45

Asp Leu Cys Glu His Phe Cys Val Pro Asn Pro Asp Gln Pro Gly Ser
    50                  55                  60

Tyr Ser Cys Met Cys Glu Thr Gly Tyr Arg Leu Ala Ala Asp Gln His
65                  70                  75                  80

Arg Cys Glu Asp Val Asp Asp Cys Ile Leu Glu Pro Ser Pro Cys Pro
                85                  90                  95

Gln Arg Cys Val Asn Thr Gln Gly Gly Phe Glu Cys His Cys Tyr Pro
            100                 105                 110

Asn Tyr Asp Leu Val Asp Gly Glu Cys Val Glu Pro Val Asp Pro Cys
        115                 120                 125

Phe Arg Ala Asn Cys Glu Tyr Gln Cys Gln Pro Leu Asn Gln Thr Ser
    130                 135                 140

Tyr Leu Cys Val Cys Ala Glu Gly Phe Ala Pro Ile Pro His Glu Pro
145                 150                 155                 160

His Arg Cys Gln Met Phe Cys Asn Gln Thr Ala Cys Pro Ala Asp Cys
                165                 170                 175

Asp Pro Asn Thr Gln Ala Ser Cys Glu Cys Pro Glu Gly Tyr Ile Leu
            180                 185                 190

Asp Asp Gly Phe Ile Cys Thr Asp Ile Asp Glu Cys Glu Asn Gly Gly
        195                 200                 205

Phe Cys Ser Gly Val Cys His Asn Leu Pro Gly Thr Phe Glu Cys Ile
    210                 215                 220

Cys Gly Pro Asp Ser Ala Leu Val Arg His Ile Gly Thr Asp Cys Asp

-continued

```
            225                 230                 235                 240
Ser Gly Lys Val Asp Gly Asp Ser Gly Ser Gly Glu Pro Pro Pro
                    245                 250                 255

Ser Pro Thr Pro Gly Ser Thr Leu Thr Pro Pro Ala Val Gly Leu Val
                    260                 265                 270

His Ser

<210> SEQ ID NO 5
<211> LENGTH: 557
<212> TYPE: PRT
<213> ORGANISM: Homo sapiens

<400> SEQUENCE: 5

Ala Pro Ala Glu Pro Gln Pro Gly Gly Ser Gln Cys Val Glu His Asp
1               5                   10                  15

Cys Phe Ala Leu Tyr Pro Gly Pro Ala Thr Phe Leu Asn Ala Ser Gln
                20                  25                  30

Ile Cys Asp Gly Leu Arg Gly His Leu Met Thr Val Arg Ser Ser Val
            35                  40                  45

Ala Ala Asp Val Ile Ser Leu Leu Leu Asn Gly Asp Gly Val Gly
    50                  55                  60

Arg Arg Arg Leu Trp Ile Gly Leu Gln Leu Pro Pro Gly Cys Gly Asp
65                  70                  75                  80

Pro Lys Arg Leu Gly Pro Leu Arg Gly Phe Gln Trp Val Thr Gly Asp
                85                  90                  95

Asn Asn Thr Ser Tyr Ser Arg Trp Ala Arg Leu Asp Leu Asn Gly Ala
            100                 105                 110

Pro Leu Cys Gly Pro Leu Cys Val Ala Val Ser Ala Ala Glu Ala Thr
        115                 120                 125

Val Pro Ser Glu Pro Ile Trp Glu Glu Gln Gln Cys Glu Val Lys Ala
130                 135                 140

Asp Gly Phe Leu Cys Glu Phe His Phe Pro Ala Thr Cys Arg Pro Leu
145                 150                 155                 160

Ala Val Glu Pro Gly Ala Ala Ala Ala Val Ser Ile Thr Tyr Gly
                165                 170                 175

Thr Pro Phe Ala Ala Arg Gly Ala Asp Phe Gln Ala Leu Pro Val Gly
            180                 185                 190

Ser Ser Ala Ala Val Ala Pro Leu Gly Leu Gln Leu Met Cys Thr Ala
        195                 200                 205

Pro Pro Gly Ala Val Gln Gly His Trp Ala Arg Glu Ala Pro Gly Ala
    210                 215                 220

Trp Asp Cys Ser Val Glu Asn Gly Gly Cys Glu His Ala Cys Asn Ala
225                 230                 235                 240

Ile Pro Gly Ala Pro Arg Cys Gln Cys Pro Ala Gly Ala Ala Leu Gln
                245                 250                 255

Ala Asp Gly Arg Ser Cys Thr Ala Ser Ala Thr Gln Ser Cys Asn Asp
            260                 265                 270

Leu Cys Glu His Phe Cys Val Pro Asn Pro Asp Gln Pro Gly Ser Tyr
        275                 280                 285

Ser Cys Met Cys Glu Thr Gly Tyr Arg Leu Ala Ala Asp Gln His Arg
    290                 295                 300

Cys Glu Asp Val Asp Asp Cys Ile Leu Glu Pro Ser Pro Cys Pro Gln
305                 310                 315                 320

Arg Cys Val Asn Thr Gln Gly Gly Phe Glu Cys His Cys Tyr Pro Asn
```

```
                    325                 330                 335
Tyr Asp Leu Val Asp Gly Glu Cys Val Glu Pro Val Asp Pro Cys Phe
                340                 345                 350

Arg Ala Asn Cys Glu Tyr Gln Cys Gln Pro Leu Asn Gln Thr Ser Tyr
            355                 360                 365

Leu Cys Val Cys Ala Glu Gly Phe Ala Pro Ile Pro His Glu Pro His
        370                 375                 380

Arg Cys Gln Met Phe Cys Asn Gln Thr Ala Cys Pro Ala Asp Cys Asp
385                 390                 395                 400

Pro Asn Thr Gln Ala Ser Cys Glu Cys Pro Glu Gly Tyr Ile Leu Asp
                405                 410                 415

Asp Gly Phe Ile Cys Thr Asp Ile Asp Glu Cys Glu Asn Gly Gly Phe
                420                 425                 430

Cys Ser Gly Val Cys His Asn Leu Pro Gly Thr Phe Glu Cys Ile Cys
            435                 440                 445

Gly Pro Asp Ser Ala Leu Val Arg His Ile Gly Thr Asp Cys Asp Ser
        450                 455                 460

Gly Lys Val Asp Gly Gly Asp Ser Gly Ser Gly Glu Pro Pro Pro Ser
465                 470                 475                 480

Pro Thr Pro Gly Ser Thr Leu Thr Pro Pro Ala Val Gly Leu Val His
                485                 490                 495

Ser Gly Leu Leu Ile Gly Ile Ser Ile Ala Ser Leu Cys Leu Val Val
            500                 505                 510

Ala Leu Leu Ala Leu Leu Cys His Leu Arg Lys Lys Gln Gly Ala Ala
        515                 520                 525

Arg Ala Lys Met Glu Tyr Lys Cys Ala Ala Pro Ser Lys Glu Val Val
    530                 535                 540

Leu Gln His Val Arg Thr Glu Arg Thr Pro Gln Arg Leu
545                 550                 555

<210> SEQ ID NO 6
<211> LENGTH: 1671
<212> TYPE: DNA
<213> ORGANISM: Homo sapiens

<400> SEQUENCE: 6
gcacccgcag agccgcagcc gggtggcagc cagtgcgtcg agcacgactg cttcgcgctc      60
tacccgggcc ccgcgacctt cctcaatgcc agtcagatct gcgacggact gcggggccac     120
ctaatgacag tgcgctcctc ggtggctgcc gatgtcattt ccttgctact gaacggcgac     180
ggcggcgttg gccgccggcg cctctggatc ggcctgcagc tgccaccgg ctgcggcgac      240 cccaagcgcc tcgggcccct gcgcggcttc cagtgggtta cgggagacaa caacaccagc     300
tatagcaggt gggcacggct cgacctcaat ggggctcccc tctgcggccc gttgtgcgtc     360
gctgtctccg ctgctgaggc cactgtgccc agcgagccga tctgggagga gcagcagtgc     420
gaagtgaagg ccgatggctt cctctgcgag ttccacttcc cagccacctg caggccactg     480
gctgtggagc ccggcgccgc ggctgccgcc gtctcgatca cctacggcac ccgttcgcg      540 gcccgcggag cggacttcca ggcgctgccg gtgggcagct ccgccgcggt ggctccctc      600 ggcttacagc taatgtgcac cgcgccgccc ggagcggtcc aggggcactg gccagggag      660 gcgccgggcg cttgggactg cagcgtggag aacggcggct gcagcacgc gtgcaatgcg      720 atccctgggg ctcccgctg ccagtgccca gccggcgccg cctgcaggc agacgggcgc      780 tcctgcaccg catccgcgac gcagtcctgc aacgacctct gcgagcactt ctgcgttccc     840
```

```
aaccccgacc agccgggctc ctactcgtgc atgtgcgaga ccggctaccg gctggcggcc       900
gaccaacacc ggtgcgagga cgtggatgac tgcatactgg agcccagtcc gtgtccgcag       960
cgctgtgtca acacacaggg tggcttcgag tgccactgct accctaacta cgacctggtg      1020
gacggcgagt gtgtggagcc cgtggacccg tgcttcagag ccaactgcga gtaccagtgc      1080
cagcccctga accaaactag ctacctctgc gtctgcgccg agggcttcgc gcccattccc      1140
cacgagccgc acaggtgcca gatgttttgc aaccagactg cctgtccagc cgactgcgac      1200
cccaacaccc aggctagctg tgagtgccct gaaggctaca tcctggacga cggtttcatc      1260
tgcacggaca tcgacgagtg cgaaaacggc ggcttctgct ccggggtgtg ccacaacctc      1320
cccggtacct tcgagtgcat ctgcgggccc gactcggccc ttgtccgcca cattggcacc      1380
gactgtgact ccggcaaggt ggacggtggc gacagcggct ctggcgagcc ccgcccagc       1440 ccgacgcccg gctccacctt gactcctccg gccgtggggc tcgtgcattc gggcttgctc      1500
ataggcatct ccatcgcgag cctgtgcctg gtggtggcgc ttttggcgct cctctgccac      1560
ctgcgcaaga agcagggcgc cgccagggcc aagatggagt acaagtgcgc ggccccttcc      1620
aaggaggtag tgctgcagca cgtgcggacc gagcggacgc cgcagagact c              1671
```